(12) United States Patent
Burkhardt

(10) Patent No.: US 8,106,200 B2
(45) Date of Patent: Jan. 31, 2012

(54) PYRIDINE BORANE COMPLEXES

(75) Inventor: Elizabeth Burkhardt, Bridgeville, PA (US)

(73) Assignee: BASF SE (DE)

( * ) Notice: Subject to any disclaimer, the term of this patent is extended or adjusted under 35 U.S.C. 154(b) by 405 days.

(21) Appl. No.: 12/441,928

(22) PCT Filed: Sep. 20, 2007

(86) PCT No.: PCT/EP2007/060003
§ 371 (c)(1),
(2), (4) Date: Mar. 19, 2009

(87) PCT Pub. No.: WO2008/034886
PCT Pub. Date: Mar. 27, 2008

(65) Prior Publication Data
US 2011/0207934 A1    Aug. 25, 2011

Related U.S. Application Data

(60) Provisional application No. 60/846,144, filed on Sep. 21, 2006.

(51) Int. Cl.
*C07F 5/02* (2006.01)
*C09K 15/32* (2006.01)

(52) U.S. Cl. ........................ 546/13; 252/400.4
(58) Field of Classification Search .......... 546/13; 252/400.4
See application file for complete search history.

(56) References Cited

U.S. PATENT DOCUMENTS
6,048,985 A    4/2000 Burkhardt et al.

FOREIGN PATENT DOCUMENTS
WO    WO-2006/020639 A2    2/2006

OTHER PUBLICATIONS

Mooney, E.F., et al., "Boron-11 chemical shifts in the determination of donor-acceptor strength—VII"; J. Inorg. Nucl. Chem.; vol. 30, 1968, pp. 1439-1446.
Pelter, A. et al.; "Borane Reagents"; Academic Press 1988, pp. 421-422.
Venugopal, B., "Ensuring Thermal Process safety. Using DSC to evaluate decomposition reactions"; Chemical processing; 2002, March issue, p. 51.
Yorke K.V., et al.; "Steroid Total Synthesis—Hydrochrysene Approach. XIV. The Synthesis of dl-18-Norepiandrosterone and dl-18-Nortestosterone"; J. Org. Chem., 1962, 27, p. 4580.
Bomann, M.D., et al."A Mild, Pyridine-Borane-Based Reductive Amination Protocol"; J. Org. Chem., 1995, 60, pp. 5995-5996.
Pelter, A.P., et al.; "Reductive Aminations of Ketones and Aldehydes using Borane-Pyridine"; J. Chem. Soc., Perkin Trans., 1984, 1, p. 717.
Brown, H.C., et al; "Molecular Addition Compounds. 9.Effect of Structure on the Reactivities of Representative Borane-Amine Complexes in Typical Reactions Such as Hydrolysis, Hydroboration, and Reduction"; Inorg. Chem. 1984, 23, pp. 2746-2753.
Jeffrey, G.H., et al.; Vogel's Textbook of Quantitative Chemical Analysis, 5th ed.; John Wiley and Sons Inc.; 1989, pp. 384-386.
Brown H.C., Organic Synthesis via Boranes, vol. 1, John Wiley and Sons Inc., 1975, p. 244.
Jeffrey, G.H, et al.; Vogel's Textbook of Quantitative Chemical Analysis, 5th ed.; John Wiley and Sons, 1989, pp. 299-300.
Nainan K.C., et al.;"A New Synthesis of Amine—and Phosphine—Boranes"; Inorganic Chemistry, vol. 8, No. 12, Dec. 1969, pp. 2671-2674.
Ryschkewitsch G.E., et al.;"Amine Boranes. Ill. Propanolysis of Pyridine Boranes"; Inorganic Chemistry; vol. 4, 1965, No. 4, Apr. 1965, pp. 575-578.
Sato S., et al.; "One-pot reductive amination of aldehydes and ketones with α-picoline-borane in methanol, in water, and in neat conditions"; Tetrahedron 60 (2004); pp. 7899-7906.

*Primary Examiner* — Charanjit Aulakh
(74) *Attorney, Agent, or Firm* — Connolly Bove Lodge & Hutz LLP

(57) ABSTRACT

The present invention relates to new borane complexes with substituted pyridines, a process for the synthesis of new borane complexes with substituted pyridines, solutions comprising new borane complexes with substituted pyridines and a method of using new borane complexes with substituted pyridines for organic reactions.

13 Claims, 1 Drawing Sheet

PYRIDINE BORANE COMPLEXES

CROSS-REFERENCE TO RELATED APPLICATIONS

This application is a national stage application (under 35 U.S.C. §371) of PCT/EP2007/060003, filed Sep. 20, 2007, which claims benefit of U.S. Provisional application 60/846,144, filed Sep. 21, 2006.

FIELD OF THE INVENTION

The present invention relates to new borane complexes with substituted pyridines, a process for the synthesis of new borane complexes with substituted pyridines, solutions comprising new borane complexes with substituted pyridines and a method of using new borane complexes with substituted pyridines for organic reactions.

BACKGROUND OF THE INVENTION

Diborane ($B_2H_6$) is a toxic and pyrophoric gas that is very readily hydrolysed and oxidised. It must be handled with utmost precautions and must be shipped and stored at temperatures below −20° C. In order to reduce the hazards of diborane, complexes of borane ($BH_3$) with donor molecules like ethers, sulfides, amines and phosphines are invariably used for organic reactions, especially for the reduction of functional groups and for hydroboration reactions with alkenes and alkynes. Functional groups reduced by such borane complexes include aldehyde, ketone, lactone, epoxide, ester, amide, oxime, imine and nitrile groups.

The most used source of borane is a tetrahydrofuran (THF) solution of the borane-THF complex, which is commercially available, usually with a concentration of 1 mol/l. However, the borane-THF complex is prone to thermal decomposition by ether cleavage of the tetrahydrofuran ring, leading to butoxyboranes and ultimately to tributylborate as decomposition products. According to U.S. Pat. No. 6,048,985, the storage stability of borane-THF complex in THF solution is increased significantly at low temperatures, even for solutions with higher concentrations.

Borane reagents with other complexing agents are available but suffer from inherent disadvantages. For example, sulfide boranes are highly concentrated but their commercial use is limited because of their strong odor. Numerous borane complexes with aliphatic and aromatic amines are known, but their reactivity is frequently not sufficient to reduce a specific functional group. Moreover, such complexing agents are sometimes difficult to remove from the reaction mixture and isolation of the desired product may become laborious.

Pyridine forms an amine borane that is not moisture sensitive and very useful for reductive aminations and reductions in protic media. Pyridine borane is commercially available and often used in acetic acid to increase the reactivity of the borane. Unfortunately, it is thermally unstable and must be kept at temperatures less than 54° C. to avoid decomposition via hydroboration/polymerization processes. Its shelf-life at ambient temperature is only 6 months. Borane complexes of pyridine, 2-n-propylpyridine, 3-methylpyridine, 3-ethylpyridine and 4-ethylpyridine are liquids which violently decompose upon distillation (Mooney E. F. et al., J. Inorg. Nucl. Chem 1968, 30, p. 1439). 2-Picoline borane (mp. 50° C.), 2-ethylpyridine borane (mp, 50-51° C.), 2,6-lutidine borane (mp. 106-107° C.) and 2,4,6-collidine borane (mp. 99-100° C.) have been isolated as solids.

It is evident that the nature of the complexing agent strongly affects the stability and reactivity of the borane reagent as well as the conditions at which a reaction can be run and the work-up procedure.

Therefore, it is desirable to develop new borane reagents with improved stability and reactivity properties and methods of using them in order to complement the range of available borane reagents and to achieve a better efficiency for organic transformations employing borane reagents.

SUMMARY OF THE INVENTION

The present invention provides new borane complexes comprising substituted pyridines as the complexing agent and solutions thereof. Another object of the present invention was the development of a process to synthesize these new borane complexes. Still another object of the present invention was the development of methods of using the new borane complexes for organic reactions.

Accordingly, new borane complexes of the formula (1) have been found,

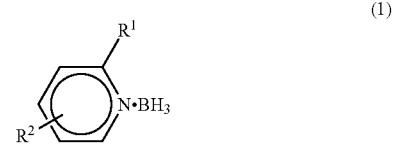

wherein
$R^1$ and $R^2$ represent independently from each other $C_1$-$C_8$-alkyl, $C_1$-$C_8$-alkoxy, $C_1$-$C_8$-alkoxy-$C_1$-$C_8$-alkyl or halogen, with the provision that $R^1$ and $R^2$ are not simultaneously methyl when $R^2$ is at the 4- or 6-position of the pyridine ring.

Furthermore, a process has been found to synthesize the new borane complexes of the formula (1), comprising the step of reacting a borane source with the respective substituted pyridine.

Another embodiment of the present invention are solutions comprising at least one of the new borane complexes of the formula (1) and at least one solvent.

The new borane complexes of the present invention can be employed for a large number of organic transformations. Examples are the reduction of functional groups and hydroboration reactions with alkenes and alkynes. Functional groups reduced by such borane complexes may for example include aldehyde, ketone, lactone, epoxide, ester, amide, oxime, imine and nitrite groups.

DETAILED DESCRIPTION OF THE INVENTION

Figure 1:
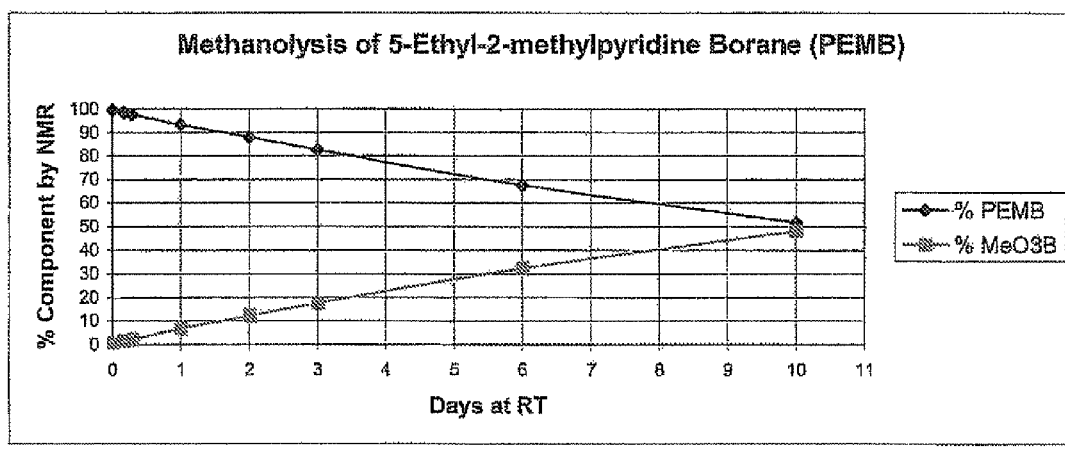
FIG. 1 illustrates the stability of 5-ethyl-2-methylpyridine borane in methanol over several days.

The new borane complexes with substituted pyridines of the present invention have chemical structures according to the general formula (1),

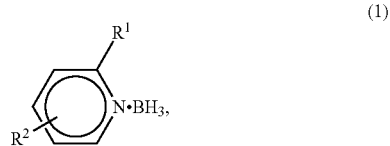

wherein
$R^1$ and $R^2$ represent independently from each other $C_1$-$C_8$-alkyl, $C_1$-$C_8$-alkoxy, $C_1$-$C_8$-alkoxy-$C_1$-$C_8$-alkyl or halogen, with the provision that $R^1$ and $R^2$ are not simultaneously methyl when $R^2$ is at the 4- or 6-position of the pyridine ring.

As used herein, the term "$C_1$-$C_8$-alkyl" denotes a branched or an unbranched saturated hydrocarbon group comprising between 1 and 8 carbon atoms. Examples are methyl, ethyl, propyl, isopropyl, n-butyl, isobutyl, sec-butyl, t-butyl, n-hexyl, n-heptyl, 2-ethylhexyl and n-octyl.

The term "$C_1$-$C_8$-alkoxy" denotes a group derived from a branched or an unbranched aliphatic monoalcohol comprising between 1 and 8 carbon atoms. Examples are methoxy, ethoxy, propoxy, isopropoxy, n-butoxy, isobutoxy and n-pentoxy.

The term "$C_1$-$C_8$-alkoxy-$C_1$-$C_8$-alkyl" denotes a $C_1$-$C_8$-alkyl group as defined above, wherein one hydrogen atom is replaced by a $C_1$-$C_8$-alkoxy group as defined above. Examples are methoxymethyl (—$CH_2OCH_3$), ethoxymethyl (—$CH_2OCH_2CH_3$) and 2-methoxyethyl (—$CH_2CH_2OCH_3$).

The term "halogen" denotes a fluorine, chlorine, bromine or iodine atom.

In a preferred embodiment of the present invention the new borane complexes have chemical structures according to the general formula (1), wherein the group $R^2$ is bonded to the 5-position of the pyridine ring.

Most preferred is an embodiment of the present invention where the new borane complex has a chemical structure according to the general formula (1), wherein the group $R^1$ is methyl and $R^2$ is bonded to the 5-position of the pyridine ring and is ethyl.

Another embodiment of the present invention is a process to synthesize the new borane complexes of the formula (1), comprising the step of reacting a borane source with the respective substituted pyridine. The borane source employed can be diborane or any other borane-containing reagent or borane-generating reaction system, that has been used for the synthesis of other borane complexes by similar processes. For example, the process of the present invention may comprise the in situ generation of borane from sodium borohydride and boron trifluoride in the presence of the respective complexing agent (cf. A. Pelter, K. Smith, H. G. Brown, "Borane Reagents", pp. 421-422, Academic Press 1988).

According to the invention, the substituted pyridine can be, for example, 2,3-lutidine, 2,5-lutidine, 5-ethyl-2-methylpyridine, 4-ethyl-2-methylpyridine, 3-ethyl-2-methylpyridine, 2,5-diethylpyridine, 5-propyl-2-methylpyridine, 4-propyl-2-methylpyridine, 5-isopropyl-2-methylpyridine, 5-t-butyl-2-methylpyridine, 5-n-hexyl-2-methylpyridine, 4-isobutyl-2-methylpyridine, 2,4-dipropylpyridine, 5-methoxymethyl-2-methylpyridine or 5-ethoxymethyl-2-methylpyridine. Preferred are pyridines with substituents $R^1$ and $R^2$ in 2- and 5-positions, most preferred is 5-ethyl-2-methylpyridine.

Another synthesis for the new borane complexes of the present invention comprises the addition of the respective substituted pyridine to a solution of borane-tetrahydrofuran complex in tetrahydrofuran. Preferably, the new borane complexes of the present invention are made in high purity by direct addition of gaseous diborane to the respective substituted pyridine. In order to allow for this reaction the diborane can be brought in contact with the respective substituted pyridine by any method, including its in situ formation, e.g. from alkali metal borohydrides. In this synthesis a stoichiometric reaction between one equivalent of diborane and two equivalents of the substituted pyridine occurs to yield two equivalents of the new borane complexes (1). Because some of the new borane complexes of the present invention are liquid at ambient temperature (e.g. 5-ethyl-2-methylpyridine borane), handling is easy and efficient large-scale synthesis can be accomplished in common reactors with stirring by adding diborane to the heat substituted pyridine.

However, the substituted pyridine may be present in excess compared to the diborane and, therefore, may serve both as complexing agent for the borane and as solvent for the newly formed borane complex. Of course, one or more other solvents with poorer complexing ability to borane than the substituted pyridine may also be present.

Another embodiment of the present invention is therefore a solution comprising at least one of the new borane complexes with substituted pyridines (1) and at least one solvent. Suitable solvents for the solutions of the present invention are at least partially miscible with the respective substituted pyridine of the borane complex (1) and inert to borane, for example ethers like diethyl ether, tetrahydrofuran or 2-methyltetrahydrofuran, sulfides like dimethyl sulfide or 1,6-thioxane or hydrocarbons like pentane, hexane, heptane, cyclohexane, toluene or xylenes. Preferred solvents for the solutions of the new complexes with substituted pyridines (1) are tetrahydrofuran, 2-methyltetrahydrofuran, dimethyl sulfide, 1,6-thioxane, toluene, hexane or cyclohexane, most preferred are tetrahydrofuran, 2-methyltetrahydrofuran, toluene, hexane or cyclohexane.

The solutions of the present invention generally contain the new borane complexes of the formula (1) in concentrations between 0.05 and 6.5 mol/l, preferably between 0.3 and 3 mol/l, more preferably between 0.5 and 2 mol/l.

The solutions of the present invention, can either be directly employed for further reactions or the borane complex can be isolated in pure form by evaporation of the solvent.

On account of the moderate reactivity of the new borane complexes with substituted pyridines (1) even solutions with protic solvents can be prepared and are stable for reasonable time periods. Therefore, reaction can be conducted in a protic environment containing water, alcohols like methanol, ethanol, propanol or isopropanol or acids like formic acid or acetic acid. As an example, FIG. 1 illustrates the stability of 5-ethyl-2-methylpyridine borane in methanol over several days.

It is well known that borane complexes tend to undergo thermal decompositions. The storage stability of the new borane complexes with substituted pyridines (1) is therefore of particular interest. Shelf-life studies performed under various conditions (0 and 20° C.) indicated that, for example, 5-ethyl-2-methylpyridine borane did not lose borane content and did not become viscous over time.

Owing to the high energy content of boranes, the energy release in thermal degradation of some of the new borane complexes of the present invention has been studied by Differential Scanning Calorimetry (DSC) and compared with the data for the commercially available amine-borane complexes. DSC is a rapid screening test useful for detecting potentially hazardous reactions and thermal decompositions. The results are summarized in Table 1.

TABLE 1

Data on Amine Borane Complexes

| Amine Name | Onset Temperature[a] (° C.) | Energy released (J/g) |
|---|---|---|
| 5-Ethyl-2-methylpyridine (60% in THF) | 188 | −361 |
| 5-Ethyl-2-methylpyridine (neat from toluene) | 202 | −570 |
| 5-Ethyl-2-methylpyridine (neat from toluene) | 192[b] | −497[b] |
| 5-Ethyl-2-methylpyridine (91% in EMP) | 199 | −512 |
| 5-Ethyl-2-methylpyridine (98%) | 205 | −600 |
| 2-Picoline (comparison) | 186 | −823 |
| 2,3-Lutidine | 198 | −600 |
| 2,6-Lutidine (comparison) | 215 | −582 |
| N,N-Diethylaniline (2 events) (comparison) | 115, 204 | −13, −35 |
| N,N-Diethylaniline (3 events) (comparison) | [b]90, 140, 345 | −10, −180, −300 |
| Pyridine (93% pyridine borane, 7% pyridine) (2 events) (comparison) | 160, 230 | −660, −225 |
| Pyridine (95% pyridine borane, 5% pyridine) (2 events) (comparison) | [b]95, 340 | −970, −190 |

[a]Temperature ramp of 4 K/min.
[b]Temperature ramp of 2.5 K/min

The measured values are not intrinsic properties but are dependent on the sensitivity of the instrument, the scanning rate and the quantity of the material (B. Venugopal, Chemical processing, 2002, March issue, p. 51). Differences in the quality of the material also have an effect, i.e. if solvent is contained, generally less energy is released. However, relative thermal risks of compounds and mixtures can be compared. From the data in Table 1 it is evident that the new 5-ethyl-2-methylpyridine borane has a higher onset temperature and releases less energy upon decomposition than pyridine borane and 2-picoline borane.

An isothermal DSC on 5-ethyl-2-methylpyridine borane (95% purity with 5% 5-ethyl-2-methylpyridine) at 150° C. showed an exothermic event after 140 minutes at this temperature. The exotherm showed an energy release of −374 J/g which is less than seen on the dynamic DSC. Another isothermal DSC was run at 125° C. which did not show any thermal events over 3000 minutes, but the dynamic scan run at the end of the isothermal scan showed an onset at 180° C. and the energy released was only −113 J/g. This lower amount of energy released is only about 20% of the energy as expected for 5-ethyl-2-methylpyridine borane, so some decomposition of 5-ethyl-2-methylpyridine borane must have occurred during the heating period. Finally, an isothermal DSC at 55° C. for 4500 minutes showed no thermal events and the dynamic scan afterwards showed the expected energy release of −658 J/g at an onset of 199° C. Compared to pyridine borane, which cannot be held at 55° C., 5-ethyl-2-methylpyridine borane is thermally more stable.

The present invention further provides a method of using the new borane complexes with substituted pyridines (1) for organic reactions. The method comprises the step of contacting a borane complex and a substrate in a reaction vessel. For most aromatic amine boranes, the reaction is expected to require heat to dissociate the borane from the amine. Preferably, the escape of eventually evolved gaseous diborane from the reaction vessel is prevented, i.e. the reaction vessel should be equipped with a back-pressure regulator and maintained at a pressure greater than approximately atmospheric pressure.

Organic reactions, for which the new borane complexes of substituted pyridines (1) can be employed according to the invention, include especially the reduction of functional groups, hydroboration reactions with alkenes and alkynes and reductive aminations of aldehydes or ketones with primary or secondary amines. Suitable substrates to be used in reduction reactions with the new borane ether complexes include organic compounds with aldehyde, ketone, oxime, imine, nitrile or carboxylic acid groups.

The reactivity of the new borane complexes with substituted pyridines (1) toward organic functional groups is expected to parallel that of pyridine borane and 2-picoline borane (cf. Yorka, K. V.; Truett, M. L; Johnson, W. S., J. Org. Chem. 1962, 27, 4580; Bomann, M. D.; Guch, I. C.; DiMare, M., J. Org. Chem. 1995, 60, 5995; Pelter, A. P.; Rosser, R. M.; Mills, S., J. Chem. Soc., Perkin Trans. 1, 1984, 717). Because of the strong interaction of borane with the nitrogen of the aromatic amine, reductions of organic functional groups benefit from the presence of acids or Lewis acids (e.g. acetic acid or boron trifluoride-diethyletherate; see Brown, H. C.; Murray, L. T. Inorg. Chem. 1984, 23, 2746f, for reactions of 2,6-lutidine borane and 2-picoline borane in acetic acid). As can be seen from examples 7 and 8, heat was required to dissociate the borane from 5-ethyl-2-methylpyridine and to induce the hydroboration of 1-octene. In the presence of acetic acid, the reaction occurs much faster and at a lower temperature (cf. example 9).

The chemoselectivity of the new borane complexes with substituted pyridines (1) in reduction reactions was investigated in a competitive reactivity study by reacting equimolar amounts of benzaldehyde and acetophenone with 5-ethyl-2-methylpyridine borane (1 equivalent of borane hydride relative to 1 equivalent of benzaldehyde, see example 10). The reaction was immediate and exothermic taking the reaction temperature to 70° C. The benzaldehyde was reduced much faster than the ketone, resulting in a 91:9 ratio of benzyl alcohol to phenethylalcohol. Of the combined carbonyl substrates, 37% was reduced and 63% remained unreduced (50% expected), which indicated that two of the three available hydride atoms were available for the reduction under these conditions. It is common that carbonyl reductions with borane frequently stop when two of the three borane hydride atoms have reacted, owing to the poor reactivity of the dialkoxyborane [(RO)$_2$BH] species formed.

The following examples illustrate the present invention without limitation of the same.

EXAMPLES

Borane concentrations were measured by two methods: iodate titration of the borane according the method described by Jeffery, G. H., Bassett, J. Mendham, J., Denney, R. C., Vogel's Textbook of Quantitative Chemical Analysis, 5$^{th}$ ed. (New York: John Wiley and Sons Inc, 1989), pp 384-386, and by boron fusion with carbonate (1:1 mixture of sodium and potassium carbonate) at 740° C. followed by dissolving the sample in concentrated hydrochloric acid and titration with sodium hydroxide in the presence of mannitol (Brown, H. C. Organic Synthesis via Boranes, Vol. 1, (New York: John Wiley and Sons Inc., 1975) p. 244) and Jeffery, G. H., Bassett, J., Mendham, J., Denney, R. C., Vogel's Textbook of Quantitative Chemical Analysis, 5$^{th}$ ed. (New York: John Wiley and Sons Inc, 1989), pp 299-300.

Example 1

Preparation of 5-ethyl-2-methylpyridine Borane from Borane-THF Complex

Borane-THF complex (20 ml of a 1M solution) was added dropwise to a solution of 5-ethyl-2-methylpyridine (2.4 g, 20 mmol) in THF (10 ml) at 4° C. The temperature of the solution rose 3 degrees during the borane addition. The $^{11}$B NMR spectrum of the solution showed a quartet at δ=−13.2 ($^1$J($^{11}$B$^1$H)=98 Hz). DSC of the solution had an exothermic event at an onset of 209° C. with an energy release of −30 J/g.

The THF was stripped off under vacuum and 40° C. to leave a brown liquid still containing about 40% THF and about 60% 5-ethyl-2-methylpyridine borane.

Example 2

Preparation of 2,3-Lutidine Borane from Borane-THF Complex

Borane-THF complex (10 ml of 1M solution) was added dropwise to a solution of 2,3-lutidine (1.07 g, 10 mmol) in THF (10 ml) at 4° C. The temperature of the solution rose 3 degrees during the borane addition. The $^{11}$B NMR spectrum of the solution showed a quartet at δ=−12.5 ($^1$J($^{11}$B$^1$H)=96 Hz). DSC of the solution had an exothermic event at an onset of 225° C. with a delta of −23 J/g.

The THF was stripped off under vacuum and 30-35° C. to leave 2,3-lutidine borane as a fluffy crystalline solid with a melting point of 120° C.

Example 3

Preparation of 5-ethyl-2-methylpyridine Borane from Diborane with Solvent

Diborane (1.4 g) was added to a solution of 5-ethyl-2-methylpyridine (12.1 g) in toluene (50 ml) to form a 2M solution of 5-ethyl-2-methylpyridine borane. The temperature of the solution rose 4 degrees during the borane addition. The $^{11}$B NMR spectrum showed a quartet at δ=−13.3 ppm ($^1$J($^{11}$B$^1$H)=98 Hz). The DSC of the solution had an onset at 212° C. and an energy release of −152 J/g. The solvent was removed under vacuum from 30 ml (27.4 g) of the solution to leave a liquid product (6.4 g, 90% yield). $^1$H NMR indicated a trace of toluene (<0.5%) remaining.

Example 4

Preparation of 5-ethyl-2-methylpyridine Borane from Diborane without Solvent Diborane (4.9 g, 177 mmol) was added to neat 5-ethyl-2-methylpyridine (45.95 g, 379 mmol) in a bottle cooled by an ice bath. The 4 h addition was exothermic. The iodate titration for borane of the product indicated 91.4% 5-ethyl-2-methylpyridine borane, which was slightly less than expected (92.5%) based on the diborane amount added. Boron fusion method indicated a purity of 91%. The density of the product was 0.909 g/ml at 25° C. Viscosity was measured at 6.6 centistokes at 20° C.

Example 5

Preparation of 5-ethyl-2-methylpyridine Borane

Diborane (21.2 g, 766 mmol) was added to neat 5-ethyl-2-methylpyridine (182.3 g, 1.504 mmol) in a bottle in an ice bath. The 2.5 h addition was exothermic raising the temperature to 6° C. The iodate titration for borane of the product indicated 93.9% 5-ethyl-2-methylpyridine borane. Boron fusion gave a value inline with the amount of diborane added, 98.9%. The $^{11}$B NMR spectrum of the solution showed a quartet at δ=−13.2 ($^1$J($^{11}$B$^1$H)=98 Hz). $^1$H NMR data (C$_6$D$_6$); δ0.70 (t, 3H, J=7.6 Hz), 1.92 (q, 2H, J=7.6 Hz), 2.51 (s, 3H), 3.4 (q, 3H, $^1$J($^{11}$B$^1$H)=98 Hz), 6.42 (d, 1H, J=7.8 Hz), 6.74 (d, 1H, J=7.8 Hz), 8.49, (s, 1H); $^{13}$C NMR (C$_6$D$_6$); δ 14.5, 21.9, 25.2, 126.2, 138.3, 148.1, 154.7, one peak missing possibly due to overlapping signals; $^{13}$C NMR (CDCl$_3$): δ 15.1, 22.2, 25.8, 127.0, 139.0, 139.7, 148.0, 155.0; IR (neat in 0.025 cm cell) B—H str. 2250-2400 cm$^{-1}$. The density was 0.900 g/ml at 23° C. Viscosity was measured at 7.2 centistokes at 20° C.

Example 6

Preparation of 5-ethyl-2-methylpyridine Borane (Diborane Addition at Ambient Temperature)

Diborane (50 g, 1.81 mol) was added to neat 5-ethyl-2-methylpyridine (461.9 g, 3.81 mol, Lonza) in a bottle at ambient temperature. The temperature rose from 20 to 26° C. during the diborane addition over 2 h 43 minutes. The iodate titration for borane indicated 91.9%. Boron fusion method of analysis gave a value as expected for the amount of diborane added, 95.8%. The $^{11}$B NMR spectrum of the solution showed a quartet at δ=−13.2 ($^1$J($^{11}$B$^1$H)=98 Hz). The density was 0.917 g/ml at 20° C. Viscosity was measured at 6.9 centistokes at 20° C. $^1$H NMR (C$_6$D$_6$): δ 0.70 (t, 3H, J=7.6 Hz), 1.92 (q, 2H, J=7.6 Hz), 2.51 (s, 3H), 3.4 (q, 3H, $^1$J($^{11}$B$^1$H)=98 Hz), 6.42 (d, 1H, J=7.8 Hz), 6.74 (d, 1H, J=7.8 Hz), 8.49 (s, 1H). Very small peaks were also seen in the $^1$H NMR spectrum due to 4-5% of free amine.

Example 7

Reaction of 5-ethyl-2-methylpyridine Borane with 1-octene (1:1)

Reaction of 5-ethyl-2-methylpyridine borane with 1-octene (1:1 mole ratio of BH$_3$ to alkene) in toluene occurred to a limited extent over 24 hours at 70° C. After heating the sample to 70° C. for 24 h, 6% of the 5-ethyl-2-methylpyridine borane had reacted based on the $^{11}$B NMR spectrum. Dialkylborane products were observed corresponding to 14% of the 1-octene reacted.

Example 8

Reaction of 5-ethyl-2-methylpyridine Borane with 1-octene (1:3)

Reaction of 5-ethyl-2-methylpyridine borane with 3 equivalents of 1-octene in toluene (1M) did not occur over 20 h at 45° C. After heating the sample to 70° C. for 24 h, 45% of the 5-ethyl-2-methylpyridine borane had reacted giving 6% trioctylborane and 39% dioctylalkoxyborane. Percent of 1-octene reacted was 45%.

Example 9

Hydroboration of 1-octene in the Presence of Acetic Acid

1-Octene (3.36 g, 30 mmol) and acetic acid (0.6 g, 10 mmol) were combined in a flask under nitrogen. 5-ethyl-2- methylpyridine borane 1.35 g, 10 mmol) was added via syringe at room temperature. No exotherm was observed and no reaction had occurred after 1 h at room temperature, as monitored by $^{11}$B NMR spectroscopy. The mixture was heated to 70° C. and monitoring continued at 1 h, 3 h and after 21 h at 70° C. 50% of the 5-ethyl-2-methylpyridine borane was consumed after 1 h (70° C.) and completely consumed after 21 h, giving, after protonation of the alkylborane, 63% triacylborane (2.7 ppm), 32% diacyloctylborane, (18 ppm) and 4% dioctylacylborane (31 ppm). The 1-octene was reduced to octane.

Example 10

Carbonyl Reduction Competition Experiment

Benzaldehyde (1.6 g, 15 mmol), acetophenone (1.8 g, 15% mmol) and acetic acid (0.3 g, 5 mmol) were combined in a flask under nitrogen. 5-Ethyl-2-methylpyridine borane (0.7 g, 5 mmol) was added via syringe over 5 minutes at room temperature. At the end of the addition the temperature of the reaction mixture reached 70° C. An ice water bath was applied immediately to bring the temperature down. The $^1$H NMR spectrum indicated that the reaction was complete, giving a 91:9 ratio of benzyl alcohol to phenethylalcohol. Of the combined carbonyl substrates, 37% were reduced and 63% remained unreduced. The $^{11}$B NMR spectrum indicated 77% borate (reduced carbonyl products) and 22% (combined species between 0 and 2 ppm) of amine coordinated to borate products.

All the references described above are incorporated by reference in its entirety for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

The invention claimed is:

1. A borane complex of the formula (1)

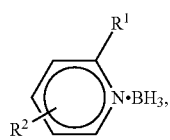

(1)

wherein $R^1$ and $R^2$ represent independently from each other $C_1$-$C_8$-alkyl, $C_1$-$C_8$-alkoxy, $C_1$-$C_8$-alkoxy-$C_1$-$C_8$-alkyl or halogen, with the provision that $R^1$ and $R^2$ are not simultaneously methyl.

2. The borane complex according to claim 1, wherein $R^2$ is bonded to the 5-position of the pyridine ring.

3. The borane complex according to claim 2, wherein $R^1$ is methyl and $R^2$ is ethyl.

4. The borane complex according to claim 1, wherein the substituted pyridine is 5-ethyl-2-methylpyridine, 4-ethyl-2-methylpyridine, 3-ethyl-2-methylpyridine, 2,5-diethylpyridine, 5-propyl-2-methylpyridine, 4-propyl-2-methylpyridine, 5-isopropyl-2-methylpyridine, 5-t-butyl-2-methylpyridine, 5-n-hexyl-2-methylpyridine, 4-isobutyl-2-methylpyridine, 2,4-dipropylpyridine, 5-methoxymethyl-2-methylpyridine or 5-ethoxymethyl-2-methylpyridine.

5. The borane complex according to claim 1, wherein the substituted pyridine is 5-ethyl-2-methylpyridine.

6. A solution comprising at least one of the borane complexes according to claim 1 and at least one solvent.

7. The solution according to claim 6, wherein the solvent comprises the substituted pyridine used to complex the borane in formula (1).

8. The solution according to claim 6, wherein the concentration of the borane complexes is between 0.05 and 6.5 mol/l.

9. The solution according to claim 8, wherein the solvent is tetrahydrofuran, 2-methyltetrahydrofuran, dimethyl sulfide, 1,6-thioxane, toluene, hexane or cyclohexane.

10. A process to synthesize the borane complex according to claim 1, comprising reacting a borane source with a substituted pyridine.

11. An organic reaction which comprises contacting the borane complex according to claim 1 with a substrate in a reaction vessel.

12. The reaction according to claim 11, wherein the organic reaction is a reduction of a functional group or a hydroboration reaction with alkenes and alkynes.

13. A method for reductive amination of an aldehyde or a ketone which comprises using a primary or secondary amine with the borane complex according to claim 1.

* * * * *